United States Patent
Lee et al.

(10) Patent No.: US 8,958,621 B2
(45) Date of Patent: Feb. 17, 2015

(54) CORNEAL GRAFT EVALUATION BASED ON OPTICAL COHERENCE TOMOGRAPHY IMAGE

(75) Inventors: Beng Hai Lee, Singapore (SG); Jun Cheng, Singapore (SG); Jiang Liu, Singapore (SG); Wing Kee Damon Wong, Singapore (SG); Ngan Meng Tan, Singapore (SG); Jodhbir Singh Mehta, Singapore (SG); Tiang Hwee Donald Tan, Singapore (SG); Tien Yin Wong, Singapore (SG)

(73) Assignees: Agency for Science, Technology and Research, Singapore (SG); Singapore Health Services Pte Ltd., Singapore (SG)

( * ) Notice: Subject to any disclaimer, the term of this patent is extended or adjusted under 35 U.S.C. 154(b) by 187 days.

(21) Appl. No.: 13/814,236

(22) PCT Filed: Aug. 3, 2011

(86) PCT No.: PCT/SG2011/000271
§ 371 (c)(1),
(2), (4) Date: Jun. 14, 2013

(87) PCT Pub. No.: WO2012/018303
PCT Pub. Date: Feb. 9, 2012

(65) Prior Publication Data
US 2013/0251230 A1 Sep. 26, 2013

(30) Foreign Application Priority Data
Aug. 3, 2010 (SG) .............................. 201005761-0

(51) Int. Cl.
G06K 9/00 (2006.01)
G06T 7/00 (2006.01)
A61B 3/10 (2006.01)
A61F 2/14 (2006.01)

(52) U.S. Cl.
CPC ............... *G06T 7/0012* (2013.01); *A61B 3/102* (2013.01); *G06T 7/0083* (2013.01); *G06T 7/0089* (2013.01); *A61F 2/142* (2013.01); *G06T 2207/10101* (2013.01); *G06T 2207/30041* (2013.01)
USPC ......................................................... 382/131

(58) Field of Classification Search
None
See application file for complete search history.

(56) References Cited

PUBLICATIONS

Yuen, Leonard H., et al. "Biometry of the cornea and anterior chamber in Chinese eyes: an anterior segment optical coherence tomography study." Investigative ophthalmology & visual science 51.7 (2010): 3433-3440.*
PCT International Search Report for PCT Counterpart Application No. PCT/SG2011/000271, 3 pgs., (Sep. 29, 2011).

(Continued)

*Primary Examiner* — Nirav G Patel
(74) *Attorney, Agent, or Firm* — Blakely, Sokoloff, Taylor & Zafman LLP

(57) ABSTRACT

An OCT image of an eye which has been subject to a DSAEK corneal transplant, in which a Descement's membrane in the cornea has been replaced by a graft, is processed to identify the outline of the graft. The process includes the steps of: computationally extracting the boundary of the cornea including the graft; computationally detecting the corners of the graft; computationally extracting points on the boundary between the graft and the original cornea; and computationally fitting the points on the boundary between the graft and the original cornea smoothly into a curve. The outline of the graft is then displayed. A graft profile may be generated, indicating the thickness of the graft at each point along its length.

11 Claims, 13 Drawing Sheets

(56) References Cited

PUBLICATIONS

PCT Written Opinion of the International Searching Authority for PCT Counterpart Application No. PCT/SG2011/000271, 4 pgs., (Sep. 29, 2011).

PCT Notification concerning Transmittal of International Preliminary Report on Patentability (Chapter I of the Patent Cooperation Treaty) for PCT Counterpart Application No. PCT/SG2011/000271, 6 pgs., (Feb. 14, 2013).

Marco Lombardo, et al., "Analysis of Posterior Donor Corneal Parameters 1 year after Descemet Stripping Automated Endothelial Keratoplasty (DSAEK) Triple Procedure", Graefe's Archive for Clinical and Experimental Ophthalmology, vol. 248, pp. 421-427, (2010).

Victor Penner, et al., "Use of the Visante for Anterior Segment Ocular Coherence Tomography", Techniques in Ophthalmology, vol. 5, No. 2, pp. 67-77, (2007).

Laurence S. Lim, et al., "Corneal Imaging with Anterior Segment Optical Coherence Tomography for Lamellar Keratoplasty Procedures", American Journal of Ophthalmology, vol. 145, No. 1, pp. 81-90, (Jan. 2008).

Mario A. Di Pascuale, et al., "Corneal Deturgescence after Descemet Stripping Automated Endothelial Keratoplasty Evaluated by Visante Anterior Segment Optical Coherence Tomography", American Journal of Ophthalmology, vol. 148, No. 1, pp. 32-37.e1, (Jul. 2009).

Xiao Chen He, et al., "Corner Detector based on Global and Local Curvature Properties", Optical Engineering, vol. 47, No. 5, pp. 057008-1-057008-12, (May 2008).

Xiang Deng, et al., "Editorial: 3D Segmentation in the Clinic: A Grand Challenge II—Liver Tumor Segmentation", MICCAI 2008 Workshop "3D Segmentation in the Clinic: A Grand Challenge II", retrieved from http://www.grand-challenge2008.bigr.nl/proceedings/liver/articles.html, 4 pgs., (Sep. 2008).

\* cited by examiner (a)

(b)

(c)

(d)

(e)

(f)

(g)

51    53                                    52

(a)

(b)

(c)

(d)

(e)

(f)

CORNEAL GRAFT EVALUATION BASED ON OPTICAL COHERENCE TOMOGRAPHY IMAGE

CROSS-REFERENCE TO RELATED APPLICATIONS

This patent application is a U.S. National Phase Application under 35 U.S.C. 371 of International Application No. PCT/SG2011/000271, filed Aug. 3, 2011, entitled CORNEAL GRAFT EVALUATION BASED ON OPTICAL COHERENCE TOMOGRAPHY IMAGE, which claims priority to Singapore Patent Application No. 201005761-0, filed Aug. 3, 2010.

FIELD OF THE INVENTION

The present invention relates to a method for processing an optical coherence tomography (OCT) image of an eye which has been subject to a corneal graft, to obtain data characterizing the image, such as data identifying the portion of the image which shows the graft.

BACKGROUND OF THE INVENTION

The cornea is a clear, transparent window of the eye. It contributes two thirds of the eye's focusing power. A healthy cornea should be clear and free of impurities. When cornea tissues are damaged or diseased, the cornea becomes cloudy and vision clarity is reduced. Cornea transplantation is a surgical procedure to replace a damaged or diseased cornea with a healthy one from a donor.

Penetrating Keratoplasty (PKP) or full thickness cornea transplantation is a procedure in which the entire cornea is completely replaced by that of a donor. The original cornea is cut away from the rest of the eye, and the replacement cornea (which has a dome shape) is attached to the remaining portion of the eye by stitches spaced apart around the circular periphery of the replacement cornea. The typical time required for visual improvement is about 6 to 12 months and a custom-made rigid contact lens has to be prescribed for the patient. The risk of rejection is about 8%. Since the cornea transplant wound (i.e. the intersection between the replacement cornea and the remaining portion of the eye) extends throughout the thickness of the replacement cornea, and along its entire circular periphery, the bond between the replacement cornea and the remaining portion of the eye is not strong and is at risk of rupture long after the operation.

An alternative to a PKP is a Descemet's Stripping Automated Endothelial Keratoplasty (DSAEK). This procedure is suitable in cases in which Descemet's membrane (which is a membrane which forms the "lower" surface of the cornea, i.e. the surface facing towards the interior of the eye) is diseased. In this procedure, as illustrated in FIG. 1, a central portion of the diseased Descemet's membrane is removed. This is illustrated in FIG. 1, which shows the eye in cross-section, so that the portion of the Descemet's membrane which is removed in a DSAEK appears as an arc. The portion of the Descemet's membrane is removed through a small incision, and replaced by a healthy one (the "graft") from a donor. The procedure retains over 90% of the patient's cornea intact and thus has a smaller risk of rejection compared to PKP. Vision improves in roughly 4 to 6 weeks and there is no need for the prescription of a rigid contact lens.

Unfortunately, there is a risk that the graft will become separated from the remaining portions of the original cornea. The graft thickness and whether it is attached properly is of utmost interest for the ophthalmologists. This can be observed using optical coherence tomography (OCT) to examine the graft after a cornea transplant is performed. OCT is a technique using near infrared light to capture 3-dimensional images, effectively behaving like "optical ultrasound". A 3-dimensional OCT image is composed of a large number of 2-dimensional images, typically scanned in a star-shape formation. FIG. 2 is an OCT image of a patient with a detached graft. The detachment can be observed very clearly. OCT images also show the graft thickness clearly and this allows early detection of possible graft rejection. Thus OCT imagery can assist ophthalmologists to make better decisions.

FIG. 3 shows Visante™ OCT Anterior Segment Imaging System available from Carl Zeiss Meditec Inc. This system provides a means for an ophthalmologist to add virtual calipers manually (i.e. by manipulating a data input device to a computer) to measure the cornea thickness. However, no depth assessment of the transplanted graft is available.

SUMMARY OF THE INVENTION

The present invention aims to provide new and useful methods and computer systems for investigating a corneal transplant using a two-dimensional OCT image (a two-dimensional slice of a 3-dimensional OCT image) of an eye which has been subject to a DSAEK corneal transplant.

In general terms, the invention proposes that an OCT image of an eye subject to a DSAEK corneal transplant in which a Descemet's membrane in a patient's cornea has been replaced by a graft, is processed to identify the outline of the graft. The process includes the steps of: computationally extracting the boundary of the body including the graft and the remaining portion of the original cornea; computationally detecting the corners of the graft; computationally extracting points on the boundary between the graft and the remaining portion of the original cornea; and computationally fitting the points on the boundary smoothly into a curve. The outline of the grant is then displayed.

As part of this process, a user may input commands to the computer system, to fine-tune the results of some or all of the steps. Specifically, the computer system may display its results including control points on the curves it generates which may be modified by the user to fine-tune the detected graft.

The invention makes possible the automated, or semi-automated, generation of a graft profile indicative of the thickness of the graft at each point along its length. To the knowledge of the present inventors, this is the first time such a profile has been available. The result of the invention may be useful as part of a process for glaucoma diagnosis.

The embodiment may additionally utilize pattern recognition, statistical learning, and other technologies.

In this document, the terms "automated" or automatically" are used to mean that, although a process may be initiated by a human operator, it subsequently runs without human involvement. The term "semi-automatically" is used to imply that although a plurality of the processing steps are performed automatically, a human operator is permitted to interact with the computer implementing the process at one or more stages, to fine-tune the operation of the embodiment, and/or its intermediate and/or final results.

The invention can be implemented in currently available instruments without extensive modifications. It may operate on OCT images obtained by an independent imaging system, and/or be incorporated into OCT imaging equipment.

BRIEF DESCRIPTION OF THE DRAWINGS

Embodiments of the invention will now be described for the sake of example only with reference to the following figures in which.

DETAILED DESCRIPTION OF THE EMBODIMENT

Figure 1:
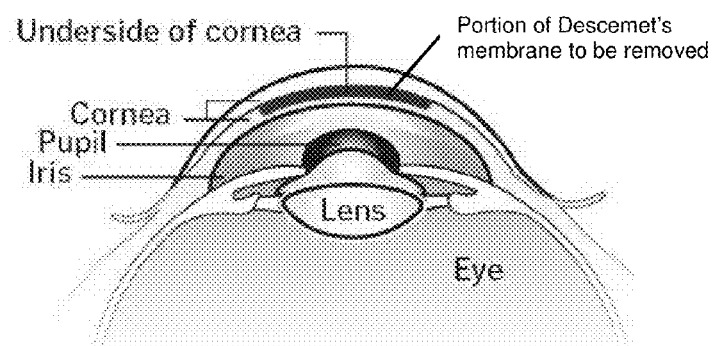
FIG. 1 is a cross-sectional view of an eye, explaining the prior art DSAEK technique.
Figure 2:
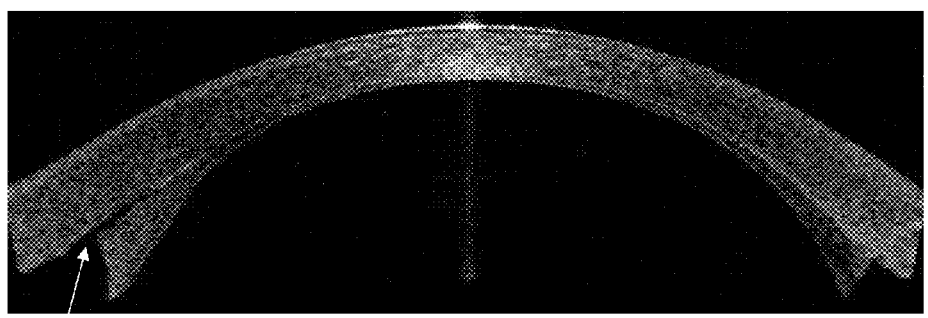
FIG. 2 is an OCT image of an eye which has been subject to the DSAEK technique.
Figure 3:
FIG. 3 shows an image generated by a prior art imaging system.
Figure 4:
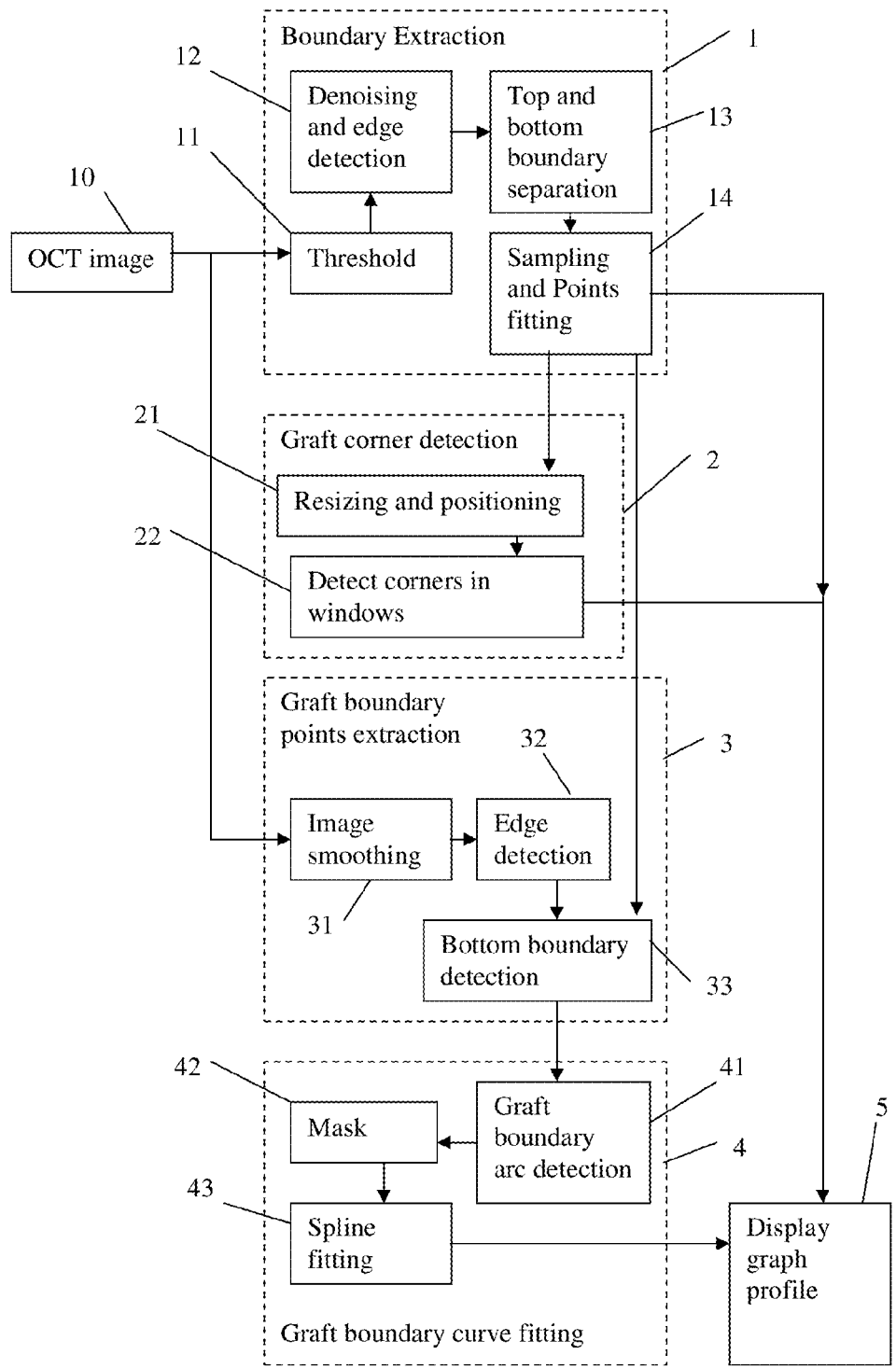
FIG. 4 is a flow diagram of a method which is an embodiment of the invention.

Referring to FIG. 4, a flow chart is given of an embodiment of the invention, known as the COLGATE (COrneaL GrAft Thickness Evaluation) system. The input to the image is a 2-dimensional OCT image 10 such as the image shown in FIG. 8(a). The image may be one slice from a 3-dimensional OCT image containing a large number of 2-d slices, e.g. scanned in a star-shape formation. The 2-dimensional OCT image is selected (e.g. manually) to contain the graft. Optionally, COLGATE can be run on each of a number of 2-dimensional OCT images sequentially.

In step 1, the embodiment extracts the boundary of the body formed by the combination of the graft and the remaining portion of the cornea. The top surface of this body is the original cornea (which is unchanged by the DSAEK), and the bottom surface of the body includes the lower surface of the graft and a portion of the lower surface of the original cornea. In step 2, the embodiment detects the corners of the transplanted graft. In step 3, the embodiment extracts points on the boundary between the graft and the remaining portion of the original cornea, and in step 4 it uses them to fit the boundary smoothly to a curve. From the outputs of steps 2, 3 and 4 the outline of the graft is identified. In step 5, the resultant graft outline is displayed, together with a graft profile indicating the thickness of the graft at each point along its length. Each of these steps can be implemented as a respective software module, typically implemented by program code operated by a general purpose computer.

Figure 5:
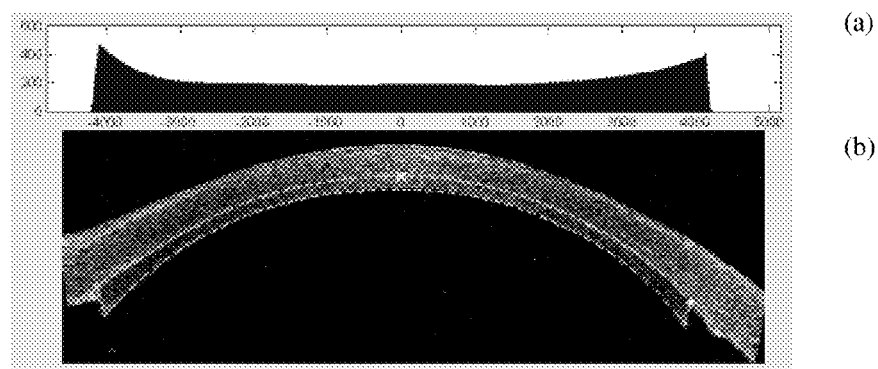
FIG. 5 is composed of FIG. 5(a) which is a graft profile produced using the embodiment of FIG. 4, and FIG. 5(b) which is a segmented graft region produced by the embodiment of FIG. 4.
Figure 6:
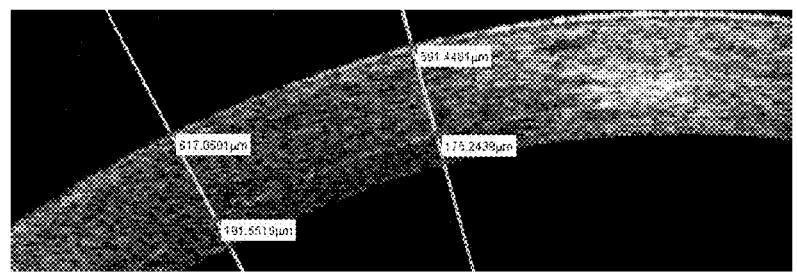
FIG. 6 shows a further image generated by the embodiment of FIG. 4, in which an OCT image is annotated with measurement data.

The graft outline may be displayed in step 5 in the form shown in FIG. 5(b). The graft profile is shown in FIG. 5(a). This is shows the thickness of the graft outline at each of a plurality of locations along its length. As described below, optionally, the user can adjust control points on the various curves to fine tune the detected graft. FIG. 6 shows an enlarged portion of an OCT image, including measurement data obtained by the embodiment, and characterizing the thickness of the subject's original cornea and the transplanted graft. These images too can be fine adjusted to fine tune the results. We now turn to a description of each of these steps in turn.

Step 1: Boundary Extraction

Figure 7:
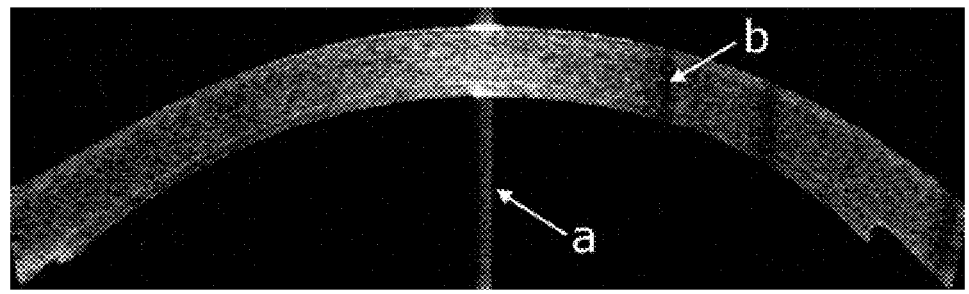
FIG. 7 illustrates two types of noise commonly found in corneal OCT images.

Step 1 involves finding the top surface of the cornea (which is unchanged by the DSAEK), and the bottom surface of the combination of the cornea and the graft. Firstly, it comprises reducing, and preferably removing, noise that is present in the OCT image 4. FIG. 7 illustrates two types of noise commonly found in corneal OCT images. A first type of noise is intensity spikes, which normally appear in the middle section of the image, such as a central intensity spike illustrated by the arrow a in FIG. 7. The other type of noise is interference noise, as illustrated by the arrow b in FIG. 7. This noise produces regions where information is missing.

Figure 8:
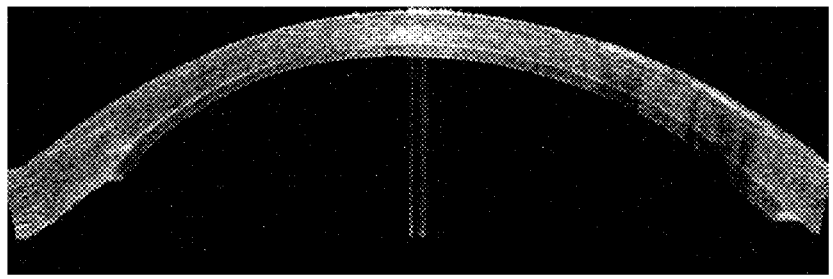
FIG. 8, which is composed of FIGS. 8(a) to 8(g), shows an image at each of certain sub-steps during a first step of the method of FIG. 4.
Figure 8:
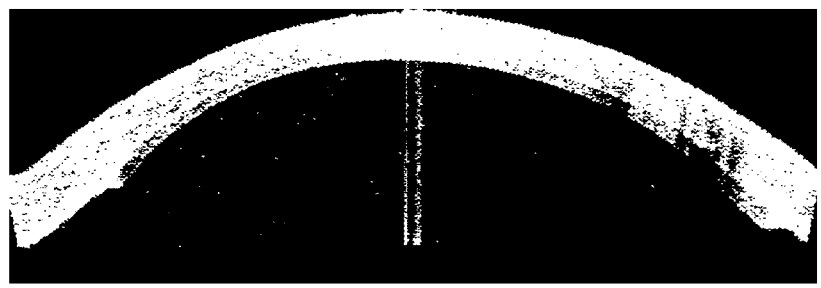
Figure 8:
Figure 8:
Figure 8:
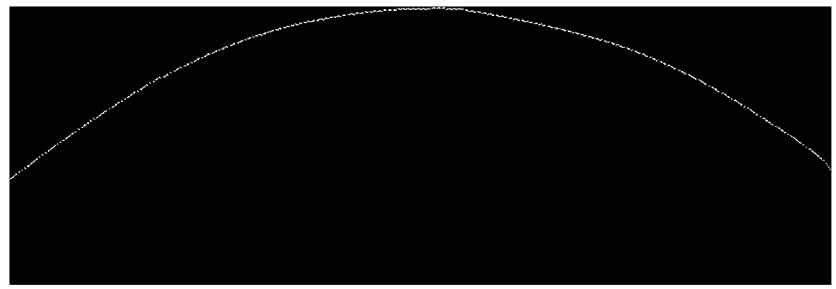
Figure 8:
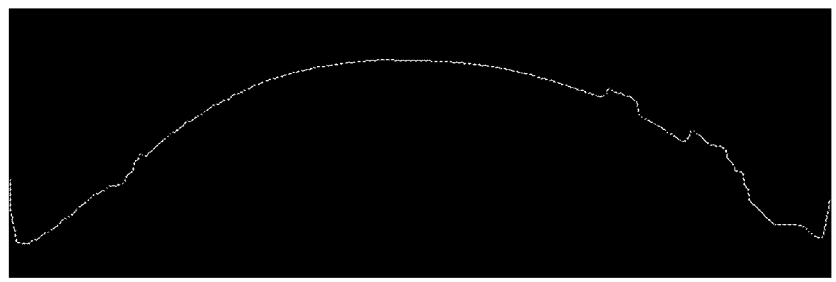
Figure 8:
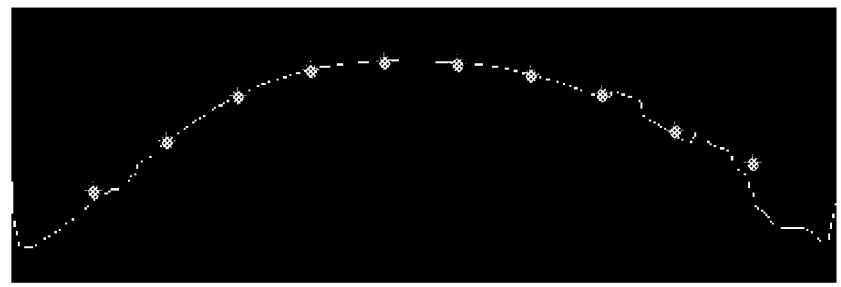

FIG. 8 shows the how the image 10 changes as it is processed in step 1. FIG. 8(a) shows the image 10 at the start of step 1. In order to segment exclude the intensity spikes, in sub-step 11 thresholding is performed on image 10 to generate a binary image, as shown in FIG. 8(b). The threshold may be chosen based on experimental data, e.g. by trial-and-error until a threshold is found at which the intensity spike disappears.

In sub-step 12, small objects are removed. In other words, we perform the steps of (i) identifying all the pixels above the threshold, (ii) identifying all islands of such pixels (i.e. objects), and (iii) setting the intensities of all the pixels of the island to zero if the number of pixels in the island is below a threshold. The threshold is selected with reference to the OCT technology which produced the images, e.g. if the OCT image is very grainy, the threshold is chosen to be larger. This produces the image of FIG. 8(c). The image is then filtered again to remove interference noise. A morphological closing process is then applied to get FIG. 8(d). Specifically, the image can be sub-sampled in order to cut down the effect of interference noise. As an example, the embodiment may sample the points in steps of 10 pixels (e.g. by taking pixel number 1, pixel number 21, pixel 31, etc) and use the result to produce a smoother curve. After the interference noise is removed, we extract the boundary using Canny Edge detection method. Alternatively we can also use other edge detection methods such as Sobel, Prewett, Roberts, etc.

In sub-step 13, the detected edge is separated into a top boundary and a bottom boundary, as shown in FIGS. 8(e) and (f) respectively. To identify the top and bottom boundary, we examine each of the columns in image FIG. 8(d), and select the top-most white point for the top boundary and the bottom-most white point as the bottom boundary. From our results, we observed that the top boundaries are generally very smooth while the bottom boundaries have some irregularities.

Then, in sub-step 14, points are sampled from the bottom boundary. Then the embodiment performs points fitting: it uses consecutive sampled points to predict the next sampling point. This is done by curve-fitting using a polynomial equation defining a curve (i.e. selecting the parameters of a polynomial equation to best fit the curve to the sampled points). The distance of each of the sampled points from the curve is measured, and those points lying too far away from the curve are replaced by corresponding predicted points, which are generated based on the curve. An image such as FIG. 8(g) is then displayed to a user, containing the bottom boundary (i.e. the remaining sampled points and the predicted points). A subset of these points are highlighted as control points, for the user to fine-tune the curve. The user is given the option to modify the bottom boundary by manipulating the control points, e.g. by dragging them across the screen using a pointer device such as a mouse or similar device. Typically, the number of control points may be 10, as shown in FIG. 8(g). If finer adjustment is required, the number of control points can be increased straightforwardly.

Step 2: Graft Corners Detection

Figure 9:
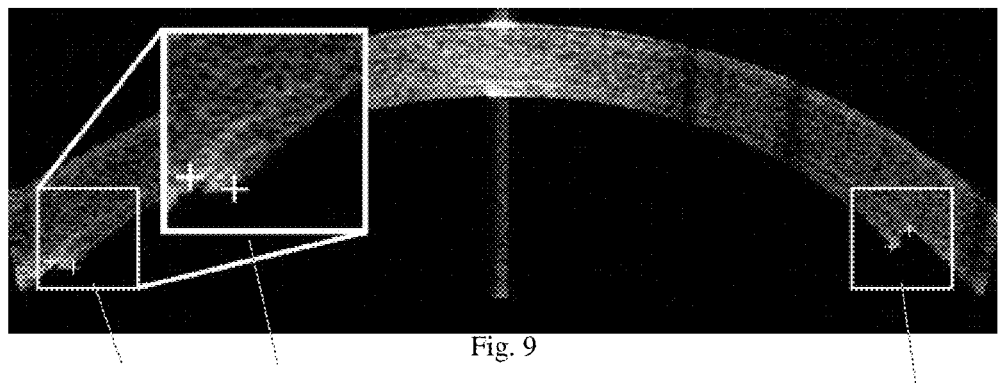
FIG. 9 illustrates an image generated by a second step of the method of FIG. 4.

Step 2 identifies the four corners of the corneal graft, as shown in FIG. 9. Corners can be detected by known corner detection algorithms based on global and local curvature properties [1]. However, the boundaries in the OCT images have rough edges, so the corner detector would tend to find false corners if the corner detection algorithms were applied to the whole OCT image. As discussed above, in the DSAEK procedure, a circular disc of the donor's Descemet's membrane is grafted to the patient's cornea. Examining the OCT images and consulting with the ophthalmologists, the present inventors have found that corner points occur at specific regions in the images. Thus, the embodiment applies the corner detector algorithms to specific windows where the corner points tend to be localized. The position and size of the two windows used are identical for all images.

To increase the chance that the windows capture the corners of the graft, the embodiment performs a resizing and positioning sub-step 21.

1. It uses the scaling factor of the OCT images (this is available for all OCT images since it is provided by the OCT image capturing device), and normalizes all images so that they all conformed to the standard scale factor.
2. Using the top boundary obtained in sub-step 14, the image is positioned so that the top-most point of the top boundary corresponds to the center of the image. This aligns the image.

FIG. 9 shows the two windows 51, 52, superimposed on an OCT image. Inset 53 is an enlarged view of the part of the OCT image within the window 51. As will be seen, the ends of the graft are indeed within the windows.

In sub-step 22, corners within the windows are detected. The four corners detected in step 2 are shown by white crosses. Any corners that are not detected within the left and right windows are simply ignored. These 4 corner points are used in step 5 to mark the ends of the graft outline.

Step 3: Graft Boundary Points Extraction

Figure 10:
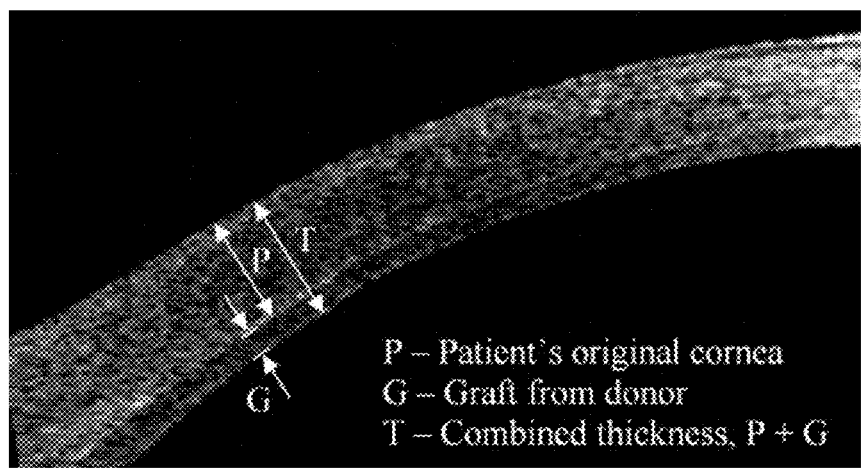
FIG. 10 is an annotated OCT image of an eye which has been subject to the DSAEK technique.
Figure 11:
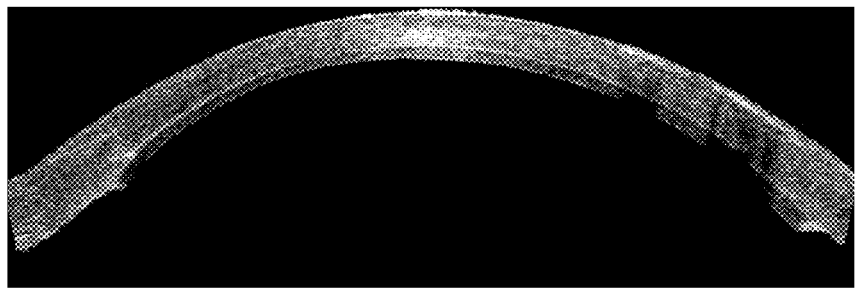
FIG. 11, which is composed of FIGS. 11(a) to 11(f), shows an image at each of certain sub-steps during a third step of the method of FIG. 4.
Figure 11:
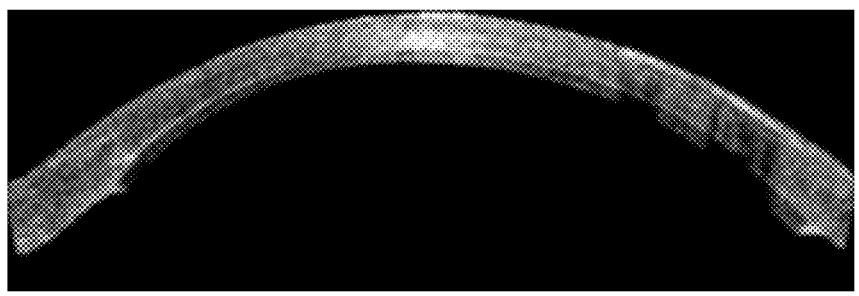
Figure 11:
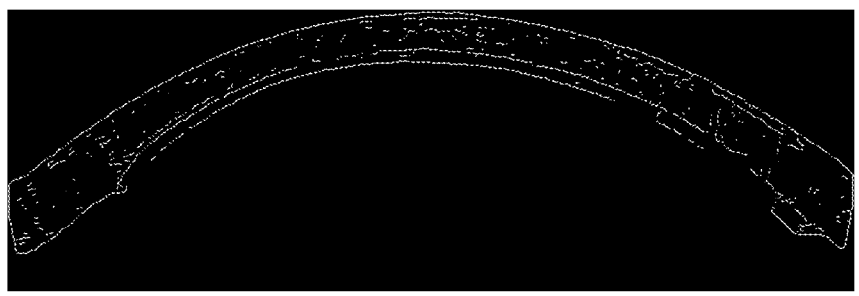
Figure 11:
Figure 11:
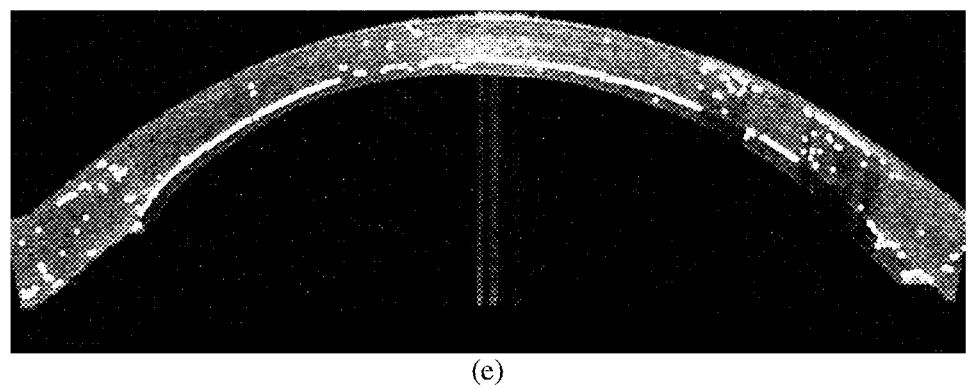
Figure 11:
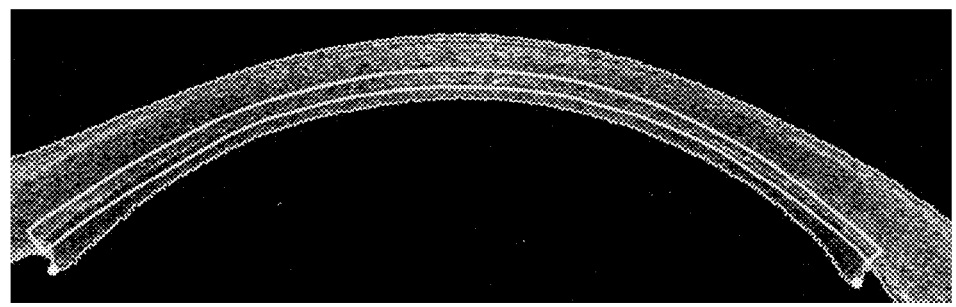

The main task in step 3 is to extract the points that lie on the boundary between the remaining portion of the patient's original cornea and the graft (i.e. the upper surface of the graft). Compared with finding the foreground boundary points in step 1, graft boundary points are more difficult to obtain because of the nature of the OCT image. For example, if we directly apply an edge detection algorithm to the OCT image, we will find the graft boundary is mixed with other edges. However, referring to FIG. 10 which shows an OCT image which has been annotated manually to indicate the locations of the graft and the remaining portion of the original cornea, it is observed that the graft boundary is visible because of contrast of the average intensities on the two sides of the image. Motivated by this, the present inventors propose that the embodiment extracts the graft boundary in the following steps. FIG. 11 shows how the image looks following each sub-step. The starting point is an image, shown in FIG. 11(a) which is the original OCT image 10 with the central spike region removed by multiplying the image 10 with a mask such as the mask of FIG. 8(d).

Sub-step 31 is a smoothing step by applying a filter, to yield FIG. 11(b). Then, in sub-step 32, there is a step of edge detection. In our implementation, the Sobel edge detection algorithm is used. FIG. 11(c) is the output of the edge detection sub-step.

In sub-step 33, the embodiment detects the bottom boundary of the remaining portion of the cornea. Firstly, the embodiment obtains a region of interest based on the top and bottom boundaries obtained in step 1. This region of interest is used as a mask to remove the edges corresponding to the top and bottom boundaries because we are interested to find the graft boundary in this step. FIG. 11(d) shows the image of FIG. 11(c) after we have masked out from it the top and bottom boundaries.

In each column in FIG. 11(d), only the bottom-most edge of FIG. 11(c) has been retained. The edges of FIG. 11(d) are plotted on FIG. 11(e) as dots, superimposed upon the original image FIG. 11(a). Some of these dots are not within the ROI. In consideration of the cornea structure (which is shaped as a portion of an ellipse due to the internal pressure of the eye) and the fact that this same internal pressure will press the graft towards the inner surface of the cornea forming a smooth elliptical contact surface, we approximate the graft boundary points as a part of ellipse. A Hough transform is applied to the dots to detect the center of the ellipse as well as the boundary of the ellipse. Then a second ROI is obtained based on the average thickness of the patient's original cornea using empirical data (available in medical publications) describing the average thickness of a cornea and its standard deviation. The thickness of the second ROI is chosen taking into account the standard deviation in cornea thickness. The result of the Hough transform gives the centre line of the second ROI, and the standard deviation gives the thickness of the ROI. This creates a ROI that is shaped like a bent tube as shown in FIG. 11(f). As explained below, in step 4, the embodiment masks out points that are outside the second ROI.

Note that a Hough transform is not the only method which can be used to define the second ROI. Besides this method, a purely empirical method can be used. Specifically, the embodiment may use a pre-known typical ratio of the values P and T (defined in FIG. 10). This typical value of P/T can be obtained in advance by a study of multiple ground truth images. The embodiment may select the second ROI based on the typical PIT ratio. For example, suppose that from studies of multiple ground truth images (that is, manually marked images) it is determined that the mean value of P/T is 70% and the standard deviation is 0.5%. In this case, the embodiment may use the top and bottom boundaries obtained above to draw a curve at a location corresponding to the 70% value. The second ROI is generated as an elongate area centered on this curve, and having a thickness of 0.5% above and below the curve. After that, only the edges within the second ROI are used.

In either case, the present embodiment uses pre-known information obtained by manual measurements to define the second ROI, discards edges outside the ROI, and then uses edge detection methods (as explained below) to further fine-tune the results. The end result is a graft boundary that may be more accurate then the one obtained above using the Hough transform.

Step 4: Graft Boundary Curve Fitting

Step 3 results in a set of boundary points corresponding to detected edges within the second ROI. Broadly speaking, step 4 locates control points which are a sub-set of the boundary points detected in step 3, and which lie on a curve describing the graft boundary.

The Graft boundary points obtained in step 3 still contain some noise, as shown in FIG. 11(e). In order to obtain a more accurate result, we approximate the graft boundary as part of an ellipse and only the boundary points near the boundary of the ellipse are retained. Specifically, in step 41, the set of boundary points is sampled, and arc detection is applied to the sampled points using the Hough transform (or a similar method) to obtain an arc. In step 42, boundary points more than a predetermined distance away from the detected arc are considered as noise and discarded. The result is shown in FIG. 12.

The corner points extracted in step 2 are used to mark the left and right ends of the graft outline.

Figure 12:
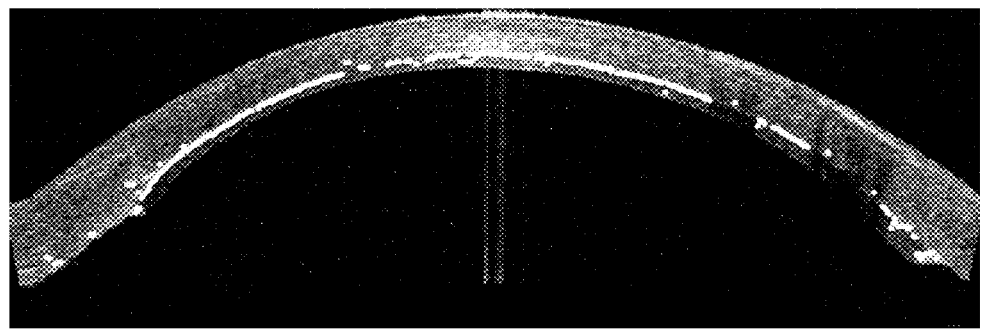
FIG. 12 shows an image produced during a fourth step of the method of FIG. 4.

In step 43, the embodiment does a similar process as in sub-step 14: down-sample the graft boundary points of FIG. 12; use consecutive sampled points to predict the next sample point, discard those which lie too far away from the predicted points, and finally fit with a spline curve. A number of control points are then sampled from the spline curve to be used a control points, so that the user can fine tune it later, e.g. by dragging the control points using a pointing device such as a mouse.

Note that in the case that there is separation between the graft and the cornea, such that there is no "boundary" as such, step 3 will detect points both on the both the upper surface of the graft and the lower surface of the cornea. Based on the points detected in step 3, the arc detection step 41 will produce a single curve. This is desirably the upper surface of the graft, so that COLGATE can delineate the graft in step 5.

Step 5: Display Graft Profile

Figure 13:
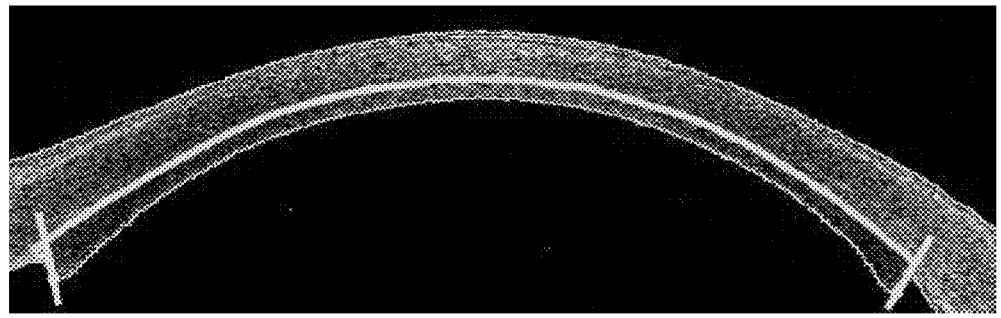
FIG. 13 shows a image produced during the fifth step of the method of FIG. 4.

Step 5 involves displaying an outline of the graft. This outline includes (i) a lower edge, which is a part of the boundary of the combination of the cornea at the graft (obtained in step 14), (ii) an upper edge which is part of the spline obtained in step 4, and (iii) left and right edge lines, which are obtained from the corners points obtained in step 2. Using the corner points, the embodiment initially forms left and right edge lines as shown in FIG. 13, but the parts of these left and right edge lines which extend beyond the lower edge and the spine (ii) are trimmed away. So are the parts of the lower edge and the spline which are to the left and right of the edge lines, thereby producing an image such as FIG. 5(b).

As well as the image 5(b), the embodiment displays a profile of the graft as shown in FIG. 5(a). You can imagine the process as bending the graft outwards so that the graft boundary (i.e. the upper edge of the graft) becomes a straight line. The center point of the cornea is marked zero, the zone on the right is marked positive, and the zone on the left is marked as negative. This gives a good and simple way to evaluate the condition of the graft. For example, a well-attached graft will eventually fuse almost perfectly with the patient's cornea, such that both ends of the graft will thin as time goes by, and this may be seen on the profile. In another example, since the function of the graft material is to destroy undesirable biological material within the cornea and thereby keep the cornea clear, excessive thinning of the entire graft may indicate a problem, since it might imply that the cells in the graft are dying.

Figure 14:
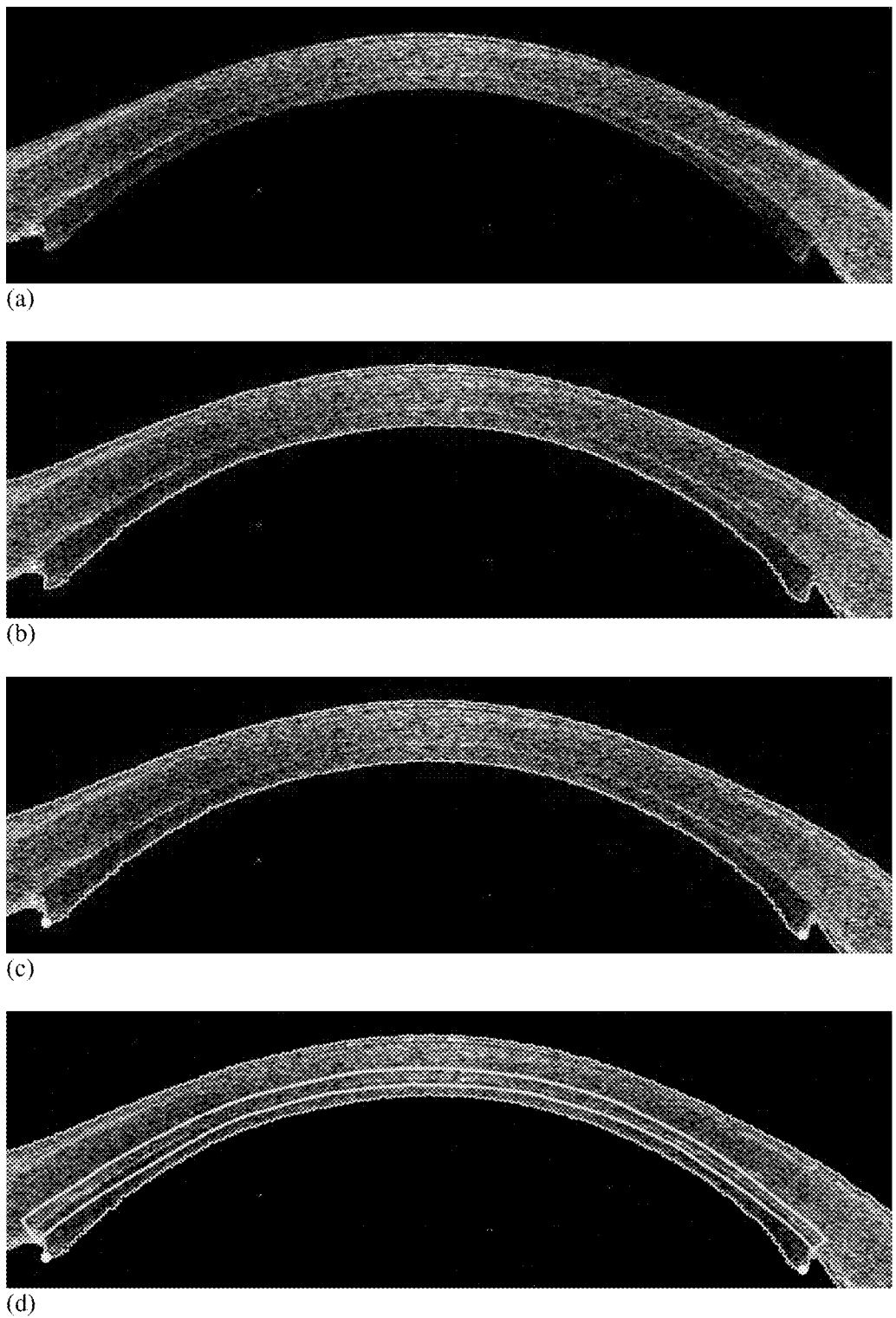
FIG. 14, which is composed of FIGS. 14(a) to 14(h) summarizes the process of FIG. 4.
Figure 14:
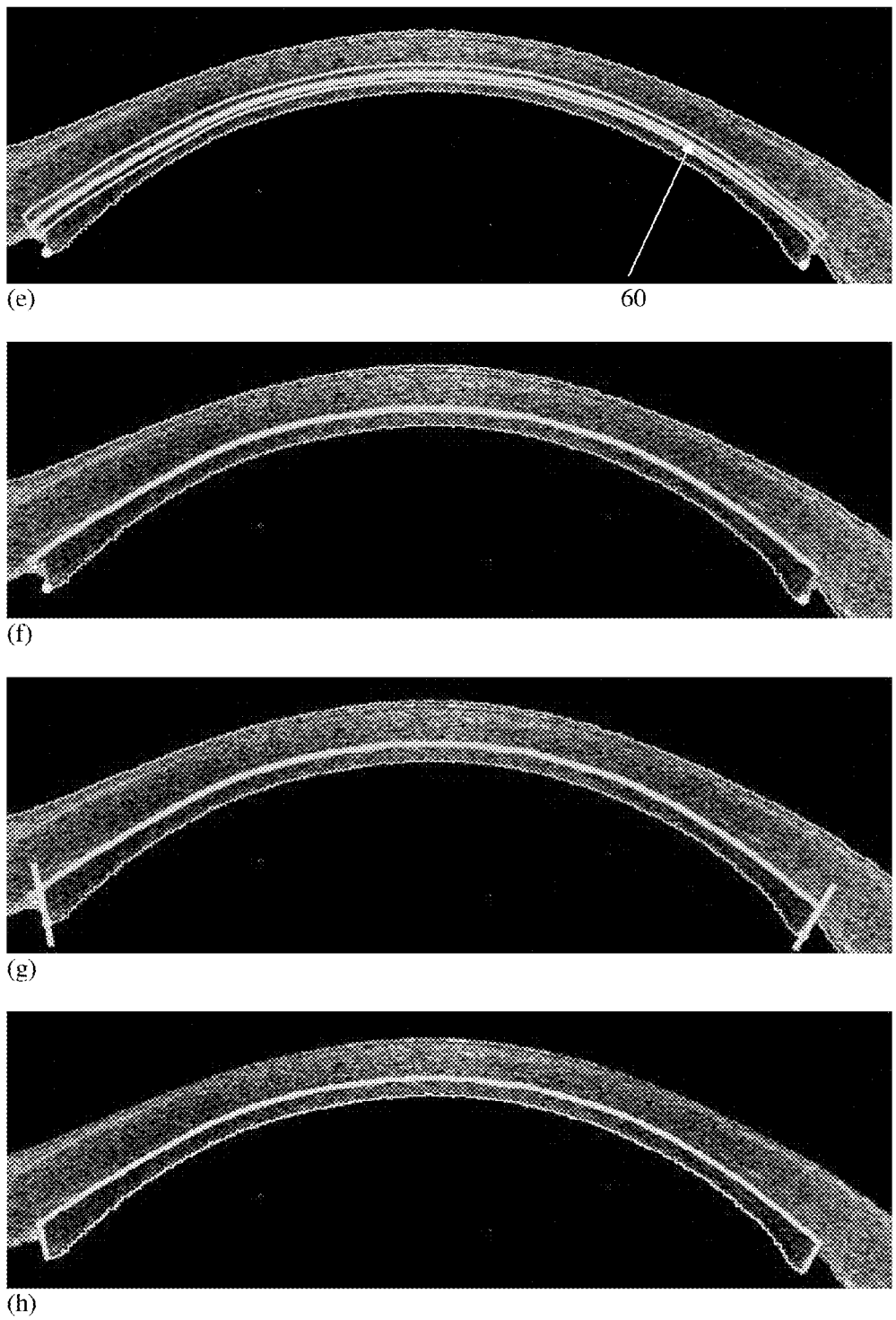

We now summarize the process of FIG. 4 with reference to FIG. 14. We start with an OCT image of the patient's cornea (FIG. 14(a)). Using the boundary extraction step 1, we mark the outline (FIG. 14(b)). In the graft corners detection step (step 2), the 4 corner points are detected (FIG. 14(c)). We then locate the region of interest (ROI) based on empirical data (FIG. 14(d), which includes the part of the ellipse obtained by the Hough transform which forms the first approximation to the graft boundary). The graft boundary points extraction step (step 4) then locates points that lies on the graft boundary. Points outside the ROI are discarded. The points are used to form a second estimate of the position of the boundary. The result is the image of FIG. 14(e), where the second estimate of the position of the boundary is shown as 60. FIG. 14(f) is an image with the ROI removed. We connect the corner points and use the result to mark the left and right edges of the graft (FIG. 14(g)). The graft is then segmented out by removing the unwanted lines (FIG. 14(h)).

4. Experiments and Results

We now present experimental results using data obtained from Singapore Eye Research Institute (SERI). They are hand picked by an ophthalmologist so as to have a good coverage of the various types of transplanted corneal grafts that are commonly encountered in DSAEK.

Figure 15:
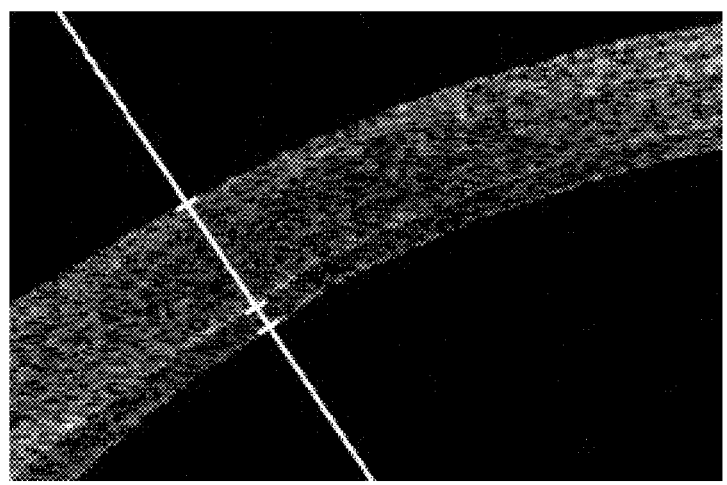
FIG. 15 indicates how ground truth images were prepared in experimental results performed to test the embodiment.

In order to mark the ground truth for the cornea thickness of the patient and graft, we performed the following procedures. A few lines were drawn on the OCT images and the 3 points of interest that intersect the line are marked as the ground truth as shown in FIG. 15. These ground truth lines were stored for each image. The embodiment was then performed, and then there was a visual comparison of the ground truth lines and the points generated by the embodiment.

To evaluate the accuracy of the lines generated by the embodiment, we adopted the metrics used in one of MICCAI grand challenge [2] and modified them for line segment evaluation. The modified metrics are as follows:

(a) Line overlap ($m_1$)

$$m_1 = \left[1 - \frac{L_g \cap L_d}{L_g \cup L_d}\right] \times 100\%$$

where $L_g$, $L_d$ are the ground truth and detected line segments respectively.

(b) Relative absolute length difference ($m_2$)

$$m_2 = \left[\frac{|D_g - D_d|}{D_g}\right] \times 100\%$$

where, and $D_g$, $D_d$ are the length of the ground truth and detected lines respectively. Note that both metrics would have value 0 for perfect detection.

Our experimental results are shown in TABLE 1. Note that the mean thickness of G (as defined by FIG. 10) is 16.6 pixels so the detection error is magnified. Overall the values look very promising.

TABLE 1

Experimental results obtained

| Thickness | Center Region | | Edge | |
|---|---|---|---|---|
| | $m_1$ | $m_2$ | $m_1$ | $m_2$ |
| T | 9.6% | 6.4% | 8.1% | 6.1% |
| P | 11.6% | 7.1% | 7.6% | 7.3% |

REFERENCES

The disclosure of the following references is incorporated by reference:

[1] X. C. He and N. H. C. Yung, "Corner detector based on global and local curvature properties", Optical Engineering, vol. 47, no. 5, pp. 057008, 2008.

[2] X. Deng, G. Hu, "Editorial: 3D Segmentation in the Clinic: A Grand Challenge II—Liver Tumor Segmentation. MICCAI 2008 Workshop "3D Segmentation in the Clinic: A Grand Challenge II". September 2008. http://grand-challenge2008.bigr.nl/proceedings/liver/articles.html

What is claimed is:

1. A method, performed on an OCT image of an eye, the eye having experienced a DSAEK corneal transplant in which a Descement's membrane in the original cornea of the eye has been replaced by a graft thereby forming a body incorporating the graft and a remaining portion of the original cornea, to identify the outline of a portion of the image corresponding to the graft, the method comprising:
   (i) computationally locating in the image the surface of the body;
   (ii) computationally locating in the image the corners of the graft;
   (iii) computationally locating boundary points in the image which are on the boundary between the graft and the remaining portion of the original cornea; and
   (iv) computationally deriving a curve fitting the boundary points,
   said outline comprising a portion of the located surface of the body, and an portion of the derived curve.

2. A method according to claim 1 in which said portion of the located surface of the body, and said portion of the derived curve are selected using the located corners of the graft.

3. A method according to claim 1 in which operation (i) is performed by seeking in each column of the image the upper and lower pixels having an intensity above a threshold.

4. A method according to claim 1 in which operation (ii) is performed by using at least one point on the surface identified in operation (i) to define the locations of two windows, the windows corresponding to respective ends of the graft, and performing an corner identification algorithm within each of the windows.

5. A method according to claim 1 in which operation (iii) is performed by an operation of edge detection, followed by removal of edges identified in operation (i) to derive a set of boundary points.

6. A method according to claim 5 in which operation (iii) further comprises generating a region of interest, and discarding any of the boundary points which are not within the region of interest, to form a reduced set of boundary points, the reduced set of boundary points being used in operation (iv).

7. A method according to claim 6 in which the region of interest is obtained by an ellipse-fitting algorithm to form an approximation of the boundary, and generating the region of interest based on the approximation of the boundary.

8. A method according to claim 1, further comprising generating, for each of a plurality of locations along the identified portion of the image corresponding to the graft, a respective thickness value indicative of the thickness of the graft, and generating a graft profile from the thickness values.

9. A method according to claim 1, further comprising receiving data input from a user to modify the located surface of the body.

10. A computer apparatus containing a processor, and a data storage device storing program instructions operative when performed by the processor to cause the processor to process an OCT image of an eye, the eye having experienced a DSAEK corneal transplant in which a Descement's membrane in the original cornea of the eye has been replaced by a graft thereby forming a body incorporating the graft and a remaining portion of the original cornea, to identify the outline of a portion of the image corresponding to the graft,
   the program instructions causing the processor:
   (i) computationally to locate in the image the surface of the body;
   (ii) computationally to locate in the image the corners of the graft;
   (iii) computationally to locate boundary points in the image which are on the boundary between the graft and the remaining portion of the original cornea; and
   (iv) computationally to derive a curve fitting the boundary points,
   said outline comprising a portion of the located surface of the body, and an portion of the derived curve.

11. A non-transitory computer program product comprising a tangible recording medium storing program instructions operative, when performed by the processor of a computer apparatus, to cause the processor to process an OCT image of an eye, the eye having experienced a DSAEK corneal transplant in which a Descement's membrane in the original cornea of the eye has been replaced by a graft thereby forming a body incorporating the graft and a remaining portion of the original cornea, to identify the outline of a portion of the image corresponding to the graft, by:
   (i) computationally locating in the image the surface of the body;
   (ii) computationally locating in the image the corners of the graft;
   (iii) computationally locating boundary points in the image which are on the boundary between the graft and the remaining portion of the original cornea; and
   (iv) computationally deriving a curve fitting the boundary points,
   said outline comprising a portion of the located surface of the body, and an portion of the derived curve.

* * * * *